US009549985B2

(12) United States Patent
Moeller et al.

(10) Patent No.: US 9,549,985 B2
(45) Date of Patent: Jan. 24, 2017

(54) COMPOSITIONS COMPRISING POLYMERS PREPARED FROM 2-HYDROXYALKYL ACIDS

(75) Inventors: Michael Moeller, Arzier (CH); Lutz Asmus, Geneva (CH); Robert Gurny, Geneva (CH)

(73) Assignee: UNIVERSITE DE GENEVE, Geneva (CH)

( * ) Notice: Subject to any disclaimer, the term of this patent is extended or adjusted under 35 U.S.C. 154(b) by 0 days.

(21) Appl. No.: 13/811,986

(22) PCT Filed: Jul. 26, 2010

(86) PCT No.: PCT/IB2010/053383
§ 371 (c)(1),
(2), (4) Date: Jan. 24, 2013

(87) PCT Pub. No.: WO2012/014011
PCT Pub. Date: Feb. 2, 2012

(65) Prior Publication Data
US 2013/0131190 A1 May 23, 2013

(51) Int. Cl.
*A61K 47/34* (2006.01)
*A61K 9/10* (2006.01)
*C08L 67/04* (2006.01)
*C08G 63/668* (2006.01)
*C08G 63/78* (2006.01)
*C08G 63/06* (2006.01)

(52) U.S. Cl.
CPC .......... *A61K 47/34* (2013.01); *A61K 9/10* (2013.01); *C08G 63/06* (2013.01); *C08G 63/668* (2013.01); *C08G 63/78* (2013.01); *C08L 67/04* (2013.01)

(58) Field of Classification Search
None
See application file for complete search history.

(56) References Cited

U.S. PATENT DOCUMENTS

| | | | | |
|---|---|---|---|---|
| 3,755,558 | A * | 8/1973 | Scribner | 424/47 |
| 5,763,405 | A * | 6/1998 | Fjellestad-Paulsen et al. | 514/10.9 |
| 5,851,451 | A * | 12/1998 | Takechi et al. | 264/4.1 |
| 5,856,401 | A * | 1/1999 | Saam | 524/800 |
| 6,245,346 | B1 * | 6/2001 | Rothen-Weinhold et al. | 424/426 |
| 6,689,768 | B2 * | 2/2004 | Oettel et al. | 514/182 |
| 7,041,320 | B1 * | 5/2006 | Nuwayser | 424/497 |
| 8,466,133 | B2 * | 6/2013 | Moller et al. | 514/152 |

FOREIGN PATENT DOCUMENTS

| | | |
|---|---|---|
| EP | 0 481 732 | 4/1992 |
| WO | WO 2007/012979 | 2/2007 |

OTHER PUBLICATIONS

Trimaille, T. et al. "Novel polymeric micelles for hydrophobic drug delivery based on biodegradable poly(hexyl-substituted lactides)" *International Journal of Pharmaceutics*, Aug. 17, 2006, pp. 147-154, vol. 319, No. 1-2.
Trimaille, T. et al. "Poly(hexyl-substituted lactides): Novel injectable hydrophobic drug delivery systems" *Journal of Biomedical Materials Research Part A*, Jan. 2007, pp. 5565, vol. 80A, No. 1.
Yin, M. et al. "Preparation and Characterization of Substituted Polylactides" *Macromolecules*, Nov. 16, 1999, pp. 7711-7718, vol. 32, No. 23.
Written Opinion in International Application No. PCT/IB2010/053883, May 13, 2011, pp. 1-8.
Schwach, G. et al. "Influence of polymerization conditions on the hydrolytic degradation of poly(DL-lactide) polymerized in the presence of stannous octoate or zinc-metal" *Biomaterials*, 2002, pp. 993-1002, vol. 23.
Asmus, L. R. et al. "Solutions as solutions—Synthesis and use of a liquid polyester excipient to dissolve lipophilic drugs and formulate sustained-release parenterals" *European Journal of Pharmaceutics and Biopharmaceutics*, 2011, pp. 584-591, vol. 79.
Asmus, L. R. et al. "In vivo biocompatibility, sustained-release and stability of triptorelin formulations based on a liquid, degradable polymer" *Journal of Controlled Release*, 2013, pp. 199-206, vol. 165.
Bachhav, Y.G. et al. "Novel micelle formulations to increase cutaneous bioavailability of azole antifungals" *Journal of Controlled Release*, 2011, pp. 126-132, vol. 153.
Di Tommaso, C. et al. "Investigations on the lyophilisation of MPEG—hexPLA micelle based pharmaceutical formulations" *European Journal of Pharmaceutical Sciences*, 2010, pp. 38-47, vol. 40.
Di Tommaso, C. et al. "Ocular biocompatibility of novel Cyclosporin A formulations based on methoxy poly(ethylene glycol)-hexylsubstituted poly(lactide) micelle carriers" *International Journal of Pharmaceutics*, 2011, pp. 515-524, vol. 416.
Di Tommaso, C. et al. "Novel micelle carriers for cyclosporin a topical ocular delivery: in vivo cornea penetration, ocular distribution and efficacy studies" *European Journal of Pharmaceutics and Biopharmaceutics*, 2012, pp. 257-264, vol. 81.
Mondon, K. et al. "MPEG-hexPLA Micelles as Novel Carriers for Hypericin, a Fluorescent Marker for Use in Cancer Diagnostics" *Photochemistry and Photobiology*, 2011, pp. 399-407, vol. 87.
Rodriguez-Aller, M. et al. "In vivo characterisation of a novel water-soluble Cyclosporine a prodrug for the treatment of dry eye disease" *European Journal of Pharmaceutics and Biopharmaceutics*, 2012, pp. 544-552, vol. 80.
Kasimova, A. O. et al. "Validation of a Novel Molecular Dynamics Simulation Approach for Lipophilic Drug Incorporation into Polymer Micelles" *The Journal of Physical Chemistry*, 2012, pp. 4338-4345, vol. 116.
Mondon, K. et al. "Novel Cyclosporin a formulations using MPEG—hexyl-substituted polylactide micelles: A suitability study" *European Journal of Pharmaceutics and Biopharmaceutics*, 2011, pp. 56-65, vol. 77.

(Continued)

*Primary Examiner* — Richard Schnizer
*Assistant Examiner* — Katherine Peebles
(74) *Attorney, Agent, or Firm* — Saliwanchik, Lloyd & Eisenschenk

(57) ABSTRACT

Described herein are compositions comprising polymers prepared by melt polycondensation of 2-hydroxyalkyl acids. Methods of making and using the compositions are also disclosed.

13 Claims, 4 Drawing Sheets

(56) References Cited

OTHER PUBLICATIONS

Di Tommaso, C. et al. "A Novel Cyclosporin a Aqueous Formulation for Dry Eye Treatment: in Vitro and in Vivo Evaluation" *Invest Ophthalmol Vis Sci.*, Apr. 2012, pp. 2292-2299, vol. 53, No. 4.
Trimaille, T. et al. "Synthesis and Properties of Novel Poly(Hexyl-Substituted Lactides) for Pharmaceutical Applications" *Chimia*, 2005, pp. 348-352, vol. 59, No. 6.
Simmons, T. et al. "Poly(phenyllactide): Synthesis, Characterization, and Hydrolytic Degradation" *Biomacromolecules*, 2001, pp. 658-663, vol. 2, No. 3.
Asmus, L. et al. "Injectable formulations for an intravitreal sustained-release application of a novel single-chain VEGF antibody fragment" *European Journal of Pharmaceutics and Biopharmaceutics*, 2015, pp. 250-260, vol. 95.

\* cited by examiner

COMPOSITIONS COMPRISING POLYMERS PREPARED FROM 2-HYDROXYALKYL ACIDS

CROSS-REFERENCE TO RELATED APPLICATION

This application is the U.S. national stage application of International Patent Application No. PCT/IB2010/053383, filed Jul. 26, 2010.

BACKGROUND

The properties of polylactide, such as the glass-transition temperature $T_g$, crystallinity, lipophilicity, and degradation time can be changed by modifying the stereochemistry of the polymer, the molecular weight, or by copolymerization with a suitable copolymer. Although polylactide can be modified for use in various applications, polylactide often forms solid aggregates that make it difficult to formulate bioactive agents with polylactide. Additionally, polylactide is not suitable for use as an injectable without formulating the polylactide as a nano- or microparticle, or without adding further excipients.

As such, a need exists for compositions that overcome the foregoing deficiencies in polymers commonly used in the art, including polylactide. These needs and other needs are satisfied by the present invention.

SUMMARY

Described herein are compositions comprising polymers prepared by melt polycondensation of 2-hydroxyalkyl acids, methods of making the compositions, and methods of using the compositions.

Disclosed are compositions comprising an admixture of a releasable agent and a polymer prepared by melt polycondensation of a substituted or unsubstituted C4-C32 2-hydroxyalkyl acid.

Also disclosed are compositions comprising an admixture of a releasable agent and a copolymer prepared by melt co-polycondensation of a substituted or unsubstituted C4-C32 2-hydroxyalkyl acid and one or more of lactic acid or glycolic acid.

Also disclosed are methods of pharmaceutical compositions, comprising combining a polymer prepared by melt polycondensation of a substituted or unsubstituted C4-C32 2-hydroxyalkyl acid with a releasable agent.

Also disclosed is a method for the preparation of poly (hydroxyalkyl acid) polymers comprising a step of melt polycondensation of one or more substituted or unsubstituted C4-C32 2-hydroxyalkyl acid(s).

Also disclosed are methods for delivering a bioactive agent to a subject, comprising administering to the subject an effective amount of a disclosed composition.

Other objects and advantages of the present invention will be apparent from the claims and the following detailed description, examples and accompanying drawings, wherein

DETAILED DESCRIPTION

Figure 1:
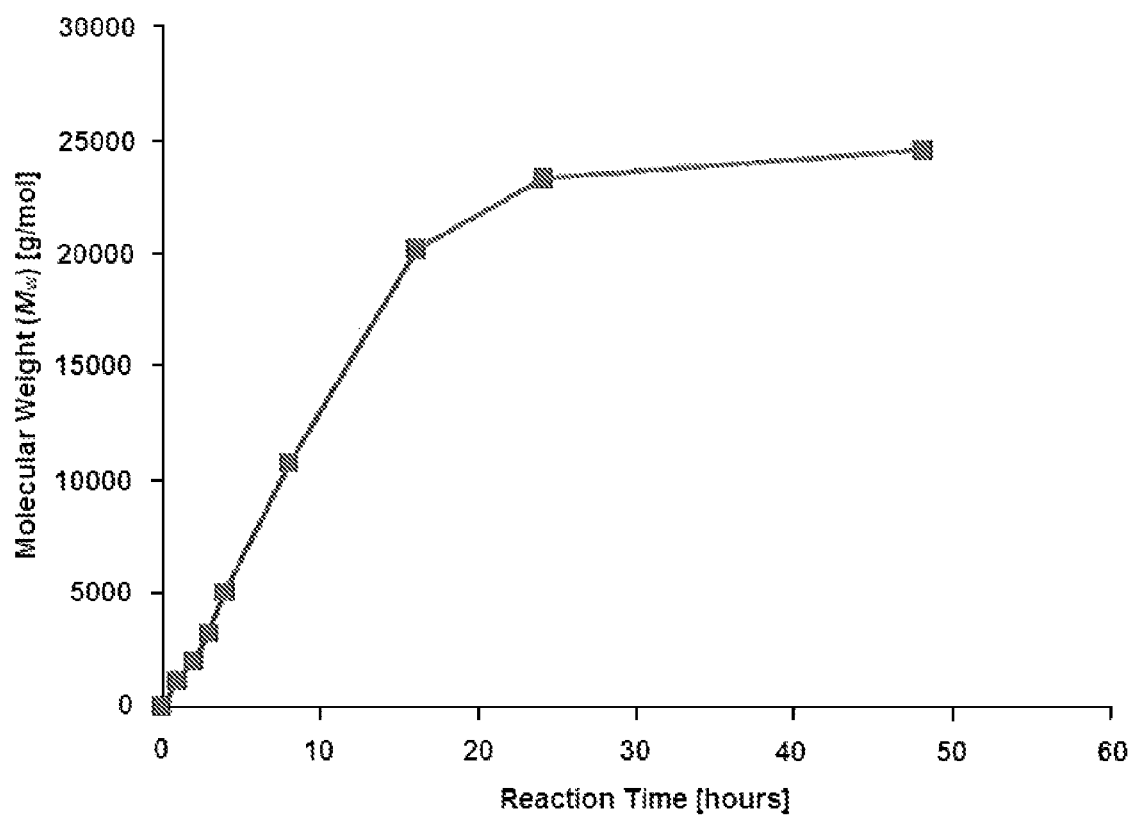
FIG. 1 is a plot of molecular weight versus reaction time for the polymerization of 2-hydroxyoctanoic acid using a tin catalyst.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

A "releasable agent" refers to an agent that can be mixed together with a disclosed polymer and subsequently released therefrom, for example, as the polymer erodes.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. A "releasable bioactive agent" is one that can be released from a disclosed polymer. Bioactive agents also include those substances which affect the structure or function of a subject, or a pro-drug, which becomes bioactive or more bioactive after it has been placed in a predetermined physiological environment.

A "polydispersity index" or "PDI" of a disclosed polymer refers to the weight averaged molecular weight ($M_w$) divided by the number averaged molecular weight ($M_n$). Both $M_w$ and $M_w$ can be readily determined by a variety of characterization techniques known in the art, including light scattering, size-exclusion chromatography (SEC), gel-permeation chromatography (GPC), viscosity measurements, among others.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

The polymers of the invention are polymers prepared from alkyl-substituted lactic acid (or 2-hydroxyalkyl acids). The polymers are prepared from linear monomers rather than ring-opening polymerization of cyclic di-lactone based monomers. Thus, the resulting compositions can be substantially free from cyclic monomers, for example, substantially free from substituted or unsubstituted lactides, glycolides or caprolactones.

The $C_4$-$C_{32}$ 2-hydroxyalkyl acid generally corresponds to the following structure:

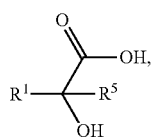

wherein $R^1$ is substituted or unsubstituted $C_2$-$C_{30}$ alkyl, and wherein $R^5$ is hydrogen or substituted or unsubstituted alkyl. For less-viscous polymers, $R^1$ is preferably at least $C_4$, so as to provide suitable hydrophobic character and reduce crystallinity of the polymer. In one aspect, $R^1$ is $C_4$-$C_{18}$. In a further aspect, $R^1$ is $C_4$ to $C_{12}$. In a specific aspect, $R^1$ is $C_6$ (hexyl-substituted lactic acid), and $R^5$ is hydrogen.

In a further aspect, the $C_4$-$C_{32}$ 2-hydroxyalkyl acid corresponds to the following structure:

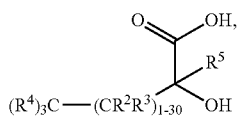

wherein each $R^2$, $R^3$, and $R^4$ is independently hydrogen, substituted or unsubstituted alkyl, alkoxy, halogen, cyano, alkyl ester, amide, or alkyl amide; and wherein $R^5$ is hydrogen or substituted or unsubstituted alkyl.

In specific aspects, the $C_4$-$C_{32}$ 2-hydroxyalkyl acid can be 2-hydroxyethanoic acid, 2-hydroxypropanoic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxypentadecanoic acid, 2-hydroxyhexadecanoic acid, 2-hydroxyheptadecanoic acid, 2-hydroxyoctadecanoic acid, 2-hydroxynonadecanoic acid, 2-hydroxyicosanoic acid, 2-hydroxyhenicosanoic acid, 2-hydroxydocosanoic acid, 2-hydroxytricosanoic acid, 2-hydroxytetracosanoic acid, 2-hydroxypentacosanoic acid, 2-hydroxyhexacosanoic acid, 2-hydroxyheptacosanoic acid, 2-hydroxyoctacosanoic acid, 2-hydroxynonacosanoic acid, 2-hydroxytriacontanoic acid, 2-hydroxyhentriacontanoic acid, or 2-hydroxydotriacontanoic acid.

In another specific aspect, the $C_4$-$C_{32}$ 2-hydroxyalkyl acid can be 2-hydroxy-2-methylpropanoic acid, 2-hydroxy-2-methylbutanoic acid, 2-hydroxy-2-ethylbutanoic acid, 2-hydroxy-2-methylpentanoic acid, 2-hydroxy-2-ethylpentanoic acid, 2-hydroxy-2-propylpentanoic acid, 2-hydroxy-2-butylpentanoic acid, 2-hydroxy-2-methylhexanoic acid, 2-hydroxy-2-ethylhexanoic acid, 2-hydroxy-2-propylhexanoic acid, 2-hydroxy-2-butylhexanoic acid, 2-hydroxy-2-pentylhexanoic acid, 2-hydroxy-2-methylheptanoic acid, 2-hydroxy-2-ethylheptanoic acid, 2-hydroxy-2-propylheptanoic acid, 2-hydroxy-2-butylheptanoic acid, 2-hydroxy-2-pentylheptanoic acid, 2-hydroxy-2-hexylheptanoic acid, 2-hydroxy-2-methyloctanoic acid, 2-hydroxy-2-ethyloctanoic acid, 2-hydroxy-2-propyloctanoic acid, 2-hydroxy-2-butyloctanoic acid, 2-hydroxy-2-pentyloctanoic acid, 2-hydroxy-2-hexyloctanoic acid, or 2-hydroxy-2-heptyloctanoic acid.

The $C_4$-$C_{32}$ 2-hydroxyalkyl acid can be obtained from commercial sources or synthesized from commercially available starting materials. For example, the $C_4$-$C_{32}$ 2-hydroxyalkyl acid can be prepared from a corresponding aldehyde according to Scheme 1.

Scheme 1.

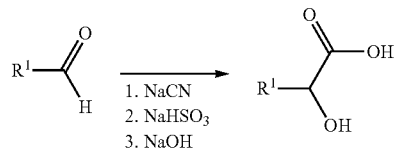

According to this procedure, the aldehyde can be added to NaHSO$_3$ in water, stirred for about 30 minutes, then a solution of NaCN (0.65 mol) in water can be added, followed by additional stirring for about 15 minutes. Upon phase separation, the upper layer can be poured directly into sulfuric acid in water and heated at about 125° C. for about 3 hours, then can be poured into NaOH in water, and stirred for about 12 h. The resultant alkaline solution can then be washed, and then acidified with HCl.

The polymer is prepared by a melt polycondensation reaction of the $C_4$-$C_{32}$ 2-hydroxyalkyl acid and thus corresponds to the following general structure:

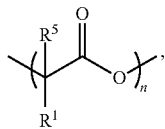

wherein $R^1$ is substituted or unsubstituted $C_2$-$C_{30}$ alkyl, wherein n is at least 2; and wherein $R^5$ is hydrogen or substituted or unsubstituted alkyl. In specific aspects, the polymer can be a polymer of any one or more of the $C_4$-$C_{32}$ 2-hydroxyalkyl acids discussed above. The $C_4$-$C_{32}$ 2-hydroxyalkyl acid can have any suitable stereochemistry. All forms of the alkyl acid, including D-, L-, or D-,L-forms can be used, such as hexyl-substituted D-lactic acid, hexyl-substituted L-lactic acid, or hexyl substituted D,L-lactic acid, for example.

The polymer can be a homopolymer of the $C_4$-$C_{32}$ 2-hydroxyalkyl acid, a copolymer of more than one $C_4$-$C_{32}$ 2-hydroxyalkyl acids as discussed above, or a copolymer of the $C_4$-$C_{32}$ 2-hydroxyalkyl acid and another hydroxy-carboxylic acid. Other acids that can be copolymerized with the $C_4$-$C_{32}$ 2-hydroxyalkyl acid include one or more of lactic acid (D- or L-), glycolic acid, 3-hydroxybutyric acid, 4-hydroxybutyric acid, 4-hydroxyvaleric acid, 5-hydroxyvaleric acid, or 6-hydroxycapronic acid, or a combination thereof. Any suitable ratio of the $C_4$-$C_{32}$ 2-hydroxyalkyl acid and one or more other acids can be copolymerized together. In one aspect, the copolymer comprises a mole ratio of about 50:50 ($C_4$-$C_{32}$ 2-hydroxyalkyl acid:other acid), about 60:40 ($C_4$-$C_{32}$ 2-hydroxyalkyl acid:other acid(s)), about 70:30 ($C_4$-$C_{32}$ 2-hydroxyalkyl acid:other acid(s)), about 80:20 ($C_4$-$C_{32}$ 2-hydroxyalkyl acid:other acid(s)), about 85:15 ($C_4$-$C_{32}$ 2-hydroxyalkyl acid:other acid(s)), about 90:10 ($C_4$-$C_{32}$ 2-hydroxyalkyl acid:other acid(s)), or about 95:5 ($C_4$-$C_{32}$ 2-hydroxyalkyl acid:other acid(s). In another aspect the copolymer can comprise a mole ratio of about 40:60 ($C_4$-$C_{32}$ 2-hydroxyalkyl acid:other acid), about 30:70 ($C_4$-$C_{32}$ 2-hydroxyalkyl acid:other acid(s)), about 20:80 ($C_4$-$C_{32}$ 2-hydroxyalkyl acid:other acid(s)), about 15:85 ($C_4$-$C_{32}$ 2-hydroxyalkyl acid:other acid(s)), about 10:90 ($C_4$-$C_{32}$ 2-hydroxyalkyl acid:other acid(s)), about 05:95 ($C_4$-$C_{32}$ 2-hydroxyalkyl acid:other acid(s)), Ratios in the region of about 10:90 ($C_4$-$C_{32}$ 2-hydroxyalkyl acid:other acid) can be of interest, for example, in the formation of biodegradable films.

The polymer can also be a block copolymer comprising a block of the $C_4$-$C_{32}$ 2-hydroxyalkyl acid, or even a $C_4$-$C_{32}$ 2-hydroxyalkyl acid copolymerized with another acid as discussed above, together with another polymer block, such as a block of a hydrophilic polymer. Specific example of hydrophilic polymer are poly(ethylene glycol) (PEG) polymers, including alkoxypoly(ethylene glycol)s such as methoxypoly(ethylene glycol) (MPEG). Examples of suitable PEG polymers include those with molecular weights of up to 5,000, such as PEG 200, PEG 400, PEG 500, PEG 1000, PEG 1500, PEG 2000, MPEG350, MPEG550, MPEG750, MPEG2000 and the like.

The block copolymers discussed above can in certain aspects exist as a micelle when dispersed in water, depending on the difference in hydrophilicity of the $C_4$-$C_{32}$ 2-hydroxyalkyl acid block and the one or more other blocks. In some aspects, a full micelle may not form, but at least partial phase separation of the blocks can exist. In some aspects, the block copolymer is emulsified, and in further aspects there may even be complete phase segregation. When the block copolymer exists as a micelle, the releasable agent (e.g., a releasable bioactive agent) can be present in the interior of the micelle. The bioactive agent can also be adsorbed or conjugated to the micelle.

Because the $C_4$-$C_{32}$ 2-hydroxyalkyl acid is polymerized using melt polycondensation, the polydispersity index (PDI) of the polymer will generally be higher than that expected for polymers prepared by ring-opening polymerization. Typically, similar polymers prepared from ring-opening polymerization have a PDI of less than 1.35, generally less than 1.2. Thus, in one aspect, the disclosed polymer has a polydispersity index (PDI) of greater than about 1.2. In a further aspect, the polymer has a polydispersity index (PDI) of at least 1.35. In a further aspect, the polymer has a polydispersity index (PDI) of at least 1.4. In a further aspect, the polymer has a polydispersity index (PDI) of at least 1.48. In a further aspect the polymer has a polydispersity index (PDI) of at least 1.6. In a further aspect the polymer has a polydispersity index (PDI) of at least 1.8, for example at least 2.0. Advantageously the polymers according to the present invention, having relatively high polydispersity index (PDI), have improved viscosity and solvent properties. In a further aspect, the polymer has a polydispersity index (PDI) of from about 1.2 to about 2.5, for example a polydispersity index (PDI) of from about 1.4 to about 2.5. In a further aspect, the polymer has a polydispersity index (PDI) of from about 1.2 to about 2.0. In a further aspect, the polymer has a polydispersity index (PDI) of from about 1.35 to about 2.0. In a further aspect, the polymer has a polydispersity index (PDI) of from about 1.4 to about 2.0, for example of from about 1.48 to about 2.0.

The polydispersity index (PDI) of the polymer prepared according to the invention can be modified to a certain extent (e.g. within a range of from about 1.2, or about 1.35, to about 2.0, or even higher) by varying polycondensation conditions, in particular by varying polymerization time, temperature, catalyst or catalyst concentration, in order to optimize viscosity and solvent properties of the polymer for a desired pharmaceutical application, for instance in order to improve injectability.

The molecular weight ($M_w$) of the polymer can vary significantly and can be up to about 60,000 Daltons. In one aspect, the polymer has an $M_w$ of at least the actual molecular weight of the $C_4$-$C_{32}$ 2-hydroxyalkyl acid dimer and up to about 60,000 Daltons. In a further aspect, the polymer has a molecular weight ($M_w$) of from 500 to 60,000 Daltons. In a further aspect, the polymer has a molecular weight ($M_w$) of from 1,000 to 60,000 Daltons. In a further aspect, the polymer has a molecular weight ($M_w$) of from 3,000 to 60,000 Daltons. In a further aspect, the polymer has a molecular weight ($M_w$) of from 10,000 to 60,000 Daltons. In a further aspect, the polymer has a molecular weight ($M_w$) of from 28,000 to 60,000 Daltons. In other aspects, the polymer can have an $M_w$ of greater than 60,000 Daltons, particularly when the polymer is present as a copolymer of the $C_4$-$C_{32}$ 2-hydroxyalkyl acid and one or more other polymers, such as a hydrophilic polymer, as discussed above.

For less viscous and even liquid compositions, the polymer preferably has a lower $M_w$, for example, less than about 15,000 Daltons. In one aspect, the polymer has an $M_w$ of less than about 10,000 Daltons. In a further aspect the polymer has an $M_w$ of less than about 8,000 Daltons, or even less than about 5,000 Daltons, for example from 500 to 5,000 Daltons. As discussed above, the polymer has a minimum molecular weight of at least the actual molecular weight of a dimer of the $C_4$-$C_{32}$ 2-hydroxyalkyl acid. In one aspect, the polymer may have a molecular weight ($M_w$) of from 500 to 15,000 Daltons, for example a molecular weight ($M_w$) of from 500 to 10,000 Daltons, for example from 1,000 to 10,000 Daltons, for example from 3,000 to 10,000 Daltons. As will be discussed below, polymers can be modified or combined with a viscosity modifier to enable their use as a less viscous and even liquid composition. Polymers can also be heated up to lower their viscosity.

Generally, the polymer can have any desirable viscosity. In one aspect, the viscosity of a neat polymer sample can be less than about 1000 Pa·s. In another aspect, the viscosity of a neat polymer sample can be less than about 500 Pa·s. In another aspect, the viscosity of a neat polymer sample can be less than about 100 Pa·s. In other aspects, the viscosity of a neat polymer sample can be from about 0.001 to about 600 Pa·s (1 cp to 60,000 cp), and preferably from about 0.1 poise to about 20 Pa·s. Viscosities can be determined using methods known in the art, such as rheometry.

The polymer has alkyl-based side chains that reduce the crystallinity of the polymer. Thus, the polymer will generally have a lower glass-transition temperature ($T_g$) than polymers prepared from lactic acid, for example. The alkyl-based side chains of the polymer essentially act as internal plasticizers, thereby reducing the crystallinity of the polymer. This property of the polymer also contributes to its ability to exist as a less viscous, or even liquid polymer. The $T_g$ of the polymer depends on a number of factors, including the exact nature of the alkyl-based side chain, the nature of any co-monomers, if present, and molecular weight, among others. In one aspect, the polymer exhibits a glass-transition temperature ($T_g$) of less than about 45° C. In a further aspect, the polymer exhibits a glass-transition temperature ($T_g$) of less than about 20° C. The polymer can also have a $T_g$ of well below 0° C. Glass transition temperatures (Tg) can be measured with a differential scanning calorimeter (DSC).

The polymer is prepared by melt polycondensation which can be carried out with or without catalyst. In one aspect, the procedure involves adding an effective amount of a catalyst to the $C_4$-$C_{32}$ 2-hydroxyalkyl acid (and any comonomers), and heating the mixture up to at least a temperature effective to melt the mixture, and maintaining this temperature for an effective amount of time to achieve polymerization (e.g., to achieve a desired degree of polymerization). An inert atmosphere and/or vacuum can be used during the polymerization. Generally, polymerization temperatures can range from above 100° C. to well over 200° C., depending on the monomer, catalyst, and other conditions. In one aspect a temperature in the range of from about 100° C. to about 250° C. may be used, for example a temperature in the range of from about 120° C. to about 200° C. Likewise, polymerization times can vary greatly from a few hours or less to over 12 hours, again depending on the desired degree of polymerization, catalyst, temperature, etc. In some aspects, it can be desirable to perform the polymerization under vacuum to support removal of water from the reaction mixture or to avoid altering the molecular weight of the polymer (and therefore viscosity) at later stages of the polymerization. Polymerization conversions and degrees of polymerizations (DP) can be determined by $^1$H NMR analysis. Molecular weights and polydispersities can be determined by gel permeation chromatography (GPC), among other methods.

In some aspects the polymerization is carried out with an effective amount of a catalyst. An effective amount of the catalyst will generally be at least 0.1 mol %, relative to the monomer(s). There is no upper limit on the amount of catalyst used. For example, if the catalyst is a benign organic acid that does not need to be removed from the polymerization mixture prior to using the composition, the amount of catalyst can be any amount that results in a desired polymer, for example, up to 10 mol % or more. In other aspects, a lower mol % catalyst can be desired, for example if the composition is desired for use as a pharmaceutical composition and the catalyst is a metallic catalyst that might be harmful in a subject or biological application above certain levels. For example in some aspects an amount of catalyst of from about 0.1 mol % to about 2.0 mol %, for example from 0.1 mol % to 1.0 mol %, for example from 0.1 mol % to 0.5 mol %, may be preferred.

A variety of catalysts can be used, and the melt polycondensation is not limited to any particular catalyst. The catalyst can be metallic, non-metallic, or enzymatic, including a variety of non-metallic organic catalysts. Suitable metal catalysts include zinc powder, tin powder, aluminum, magnesium and germanium, metal oxides such as tin oxide (II), antimony oxide (III), zinc oxide, aluminum oxide, magnesium oxide, titanium oxide (IV) and germanium oxide (IV), metal halides such as tin chloride (II), tin chloride (IV), tin bromide (II), tin bromide (IV), antimony fluoride (III), antimony fluoride (V), zinc oxide, magnesium chloride and aluminum chloride, sulfates such as tin sulfate (II), zinc sulfate and aluminum sulfate, carbonates such as magnesium carbonate and zinc carbonate, borates such as zinc borates, organic carboxylates such as tin acetate (II), tin octanoate (II), tin lactate (II), zinc acetate and aluminum acetate, organic sulfonates such as tin trifluoromethane sulfonate (II), zinc trifluoromethane sulfonate, magnesium trifluoromethane sulfonate, tin (II) methane sulfonate and tin (II) p-toluene sulfonate. Dibutyltin dilaurate (DBTL), $Sb_2O_3$, Ti(IV)bu, Ti(IV)iso, and others. Tin catalysts, and other metallic catalysts have been widely used in ring-opening polymerisation techniques, and the use of tin, or other metallic, catalysts is known to leave residual amounts of tin, or other metal, in the polymer product (see for example, G. Schwach et al., *Influence of polymerization conditions on the hydrolytic degradation of poly(DL-lactide) polymerized in the presence of stannous octoate or zinc-metal*, Biomaterials, 23 (2002) 993-1002).

For some applications, a potential drawback in the use of tin catalysts or other metallic catalysts is the risk of presence of residual amounts of metal catalyst or deriving metal salts, where the presence of even trace amounts of such metals or deriving metal salts may potentially have deleterious effects in pharmaceutical application. Another potential drawback of the use of tin catalysts, or other metallic catalysts, is the necessity for the use of organic solvents for the removal of the catalyst.

In some aspects, the catalyst is non-metallic, and thus the composition is substantially free from metal. In other aspects, the catalyst is a non-tin catalyst, and thus the composition is substantially free from tin. Such compositions can be desirable in pharmaceutical applications in which metal can have a deleterious effect. Non-metallic acids include a variety of inorganic and organic acids. The acid can be a weak acid or a strong acid. In some instances, the organic acid need not be removed from the composition prior to use. Weak acids can be preferred when the acid catalyst will not be removed from the composition. Examples of organic acids include acetic acid, glacial acetic acid, methane sulfonic acid, ethane sulfonic acid, 1-propane sulfonic acid, 1-butane sulfonic acid, trifluoromethane sulfonic acid, benzene sulfonic acid, p-toluene sulfonic acid, p-xylene-2-sulfonic acid, naphthalene-1-sulfonic acid and naphthalene 2-sulfonic acid, and others. Acetic acid and glacial acetic acid, amongst others, which have FDA GRAS (Generally Recognized As Safe) designation, may be of particular interest when the catalyst will not be removed from the composition.

Examples of suitable inorganic acids include acids such as, sulfuric acid, sulfurous acid, phosphoric acid, phosphonic acid and others. In one aspect the catalyst is an inorganic acid. In a particular aspect the catalyst is sulfuric acid.

In some aspects the polymerization is effected without a catalyst. Advantageously, use of a catalyst-free process avoids the need for any step of purification for removal of the catalyst, thereby further simplifying the process, and the resulting polymers are free of any residual catalyst. Accordingly, polymers prepared by the polycondensation process of the invention in the absence of a catalyst can be of particular interest for pharmaceutical applications.

Generally, the composition comprising the polymer and the releasable agent can be a liquid, solid, semi-solid, or gel. In some aspects, the composition is a liquid. Such compositions are useful as injectable compositions, or flowable compositions. In other aspects, viscosity modifiers, plasticizers, or other additives or excipients can be added to the composition to change the viscosity of the composition, or even make the composition liquid when it would otherwise be solid, as discussed below. The releasable agent can be dissolved, dispersed, or otherwise mixed with the polymer and/or other additives and excipients, if present. In other aspects, the releasable agent can be contained within the polymer, for example, when the polymer is a micelle or has phase segregated morphology.

The composition can be applied to a number of subjects, plants, or articles and thereafter release the releasable agent onto or into the desired location. Thus, in various aspects, the composition can be injected, for example, injected into a subject, sprayed, for example, sprayed onto a plant, rubbed, painted, spin-cast, or otherwise applied.

The composition comprising the polymer and the releasable agent can in various aspects comprise other components, such as viscosity modifiers. Examples of viscosity modifiers include plasticizers, additives, and solvents. Solvents can be used to formulate the releasable agent with the polymer if desired. These solvents can remain in the composition if desired. The amount of other components, such as viscosity modifiers, that can be present in the composition can vary and will generally be less than about 50% by weight of the composition. In one aspect the viscosity modifier is present in an amount of from a trace amount up to 50% by weight of the composition. In a further aspect the viscosity modifier is present in an amount of from a trace amount up to 25% by weight of the composition. In a further aspect the viscosity modifier is present in an amount of from a trace amount up to 20% by weight of the composition. In a further aspect the viscosity modifier is present in an amount of from a trace amount up to 15% by weight of the composition. In a further aspect the viscosity modifier is present in an amount of from a trace amount up to 10% by weight of the composition. In a further aspect the viscosity modifier is present in an amount of from a trace amount up to 5% by weight of the composition. In a further aspect the viscosity modifier is present in an amount of from a trace amount up to 1% by weight of the composition. A trace amount refers to about 1% or less, for example, 0.1%, 0.2%, or 0.5%.

A variety of additives can be used in combination with the compositions, such as a water-soluble polymer such as polyethylene glycol, a protein, polysaccharide, or carboxmethyl cellulose, a surfactant, a plasticizer, a high- or low-molecular-weight porosigen such as polymer or a salt or sugar, or a hydrophobic low-molecular-weight compound such as cholesterol or a wax. In some aspects, N-methylpyrrolidone (NMP) can be added to modify the viscosity of the polymer. Other components such as, for example, excipients, pharmaceutically acceptable carriers or adjuvants, microparticles, and the like, can be combined with the compositions, or be present in a composition.

In some aspects another polymer prepared by melt polycondensation or melt co-polycondensation of a substituted or unsubstituted $C_4$-$C_{32}$ 2-hydroxyalkyl acid, having a lower molecular weight, and a lower viscosity, can be added to the composition to modify the viscosity of the polymer of the composition.

A variety of other polymers can be used in combination with the polymers of the invention and can be present in the compositions. Examples include polyglycolide (PG), polylactide (PL), polycaprolactone (PCL), polyethylene glycol (PEG), polydioxanone (PDO), poly(D,L-lactide-co-glycolide) (D,L-PLG) and poly(L-lactide-co-glycolide) (L-PLG), poly(hydroxyl alkanoate) (PHA), and other biodegradable and biocompatible polymers. Biocompatible polymers that can be used include polyesters, polyethers, polyanhydrides, polyamines, poly(ethylene imines) polyamides, polyesteramides, polyorthoesters, polydioxanones, polyacetals, polyketals, polycarbonates, polyphosphoesters, polybutylene, polyterephthalate, polyorthocarbonates, polyphosphazenes, polyurethanes, polytetrafluorethylenes (PTFE), polysuccinates, poly(malic acid), poly(amino acids), polyvinylpyrrolidone, polyhydroxycellulose, polysaccharides, chitin, chitosan, hyaluronic acid, and copolymers, terpolymers and mixtures thereof. Synthetic polymers and/or natural polymers can be used as the second polymer in combination with the polymers of the invention. The polymers can be admixed together, or otherwise used in combination.

When the polymers are used in combination with other lactide-based polymers, the lactide-based polymers can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be made by ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

In some aspects, as briefly discussed above, it can be desirable to contact or admix a disclosed polymer with one or more plasticizers, in order to alter the physical properties (e.g., lower the $T_g$ or $T_m$) of the resulting composition.

Plasticizers that can be used include all FDA approved, or GRAS designated, plasticizers, such as benzyl benzoates, cellulose acetates, cellulose acetate phthalates, chlorobutanol, dextrines, dibutyl sebacate, dimethyl sebacate, acetyl phthalates, diethyl phthalate, dibutyl phthalate, dipropyl phthalate, dimethyl phthalate, dioctyl phthalate, methyl cellulose, ethyl cellulose, hydroxyethyl cellulose, hydroxypropyl cellulose, hydroxypropyl methyl celluloses, gelatine, glycerines, glyceryl monostearate, monoglycerides, mono- and di-acetylated monoglycerides, glycerol, mannitol, mineral oils and lanolin alcohols, petrolatum and lanolin alcohols, castor oil, vegetable oils, coconut oil, polyethylene glycol, polymethacrylates and copolymers thereof, polyvinyl-pyrrolidone, propylene carbonates, propylene glycol, sorbitol, suppository bases, diacetine, triacetin, triethanolamine, esters of citric acid, triethyl citrate, acetyl triethyl citrate, acetyl tributyl citrate, triethyl citrate, and esters of phosphoric acid, NMP, DMSO, and FDA GRAS designated oils such as vegetable oils including sesame oil, peanut oil, olive oil, amongst others.

A composition comprising the polymer and one or more viscosity modifiers can have any desirable viscosity. In some aspects, such a composition can have a viscosity of from about 0.001 to about 200 Pa·s, preferably from about 0.001 to about 50 Pa·s, more preferably from about 0.001 to about 20 Pa·s (1 cP to 20,000 cP), and more preferably from about 0.1 Pa·s to about 20 Pa·s. Thus, the polymer in neat form can have any suitable viscosity, and such a polymer can be combined with a viscosity modifier to provide a composition having a desired viscosity, such as a viscosity suitable for an injectable composition.

The polymer can erode and allows the agent in the composition to be released. The polymer can also be biocompatible or biodegradable, and thus the polymer can erode in a biological fluid or tissue. A variety of releasable agents can be used in the compositions. Generally, any agent for which release over time is desired can be used. Thus, the releasable agent can be a bioactive agent, cosmetic substance, such as a lotion, or other substance, such as an agricultural product. The releasable agent can be dissolved or dispersed in the polymer and can be present in any suitable amount, which will generally depend on the intended use of the composition. In a particular aspect the releasable agent is dissolved in the polymer.

In one specific aspect, the releasable agent is a bioactive agent. A large variety of bioactive agents can be used with the compositions. The bioactive agent can be blended, admixed, or otherwise combined with the polymer. In one aspect, the bioactive agent can be preformulated, e.g., spray-dried with sugar, into a defined particle. In one aspect the bioactive compound can be fully dissolved in the polymer. In another aspect, at least a portion of the bioactive agent can be dissolved in the polymer. In a further aspect, at least a portion of the bioactive agent can be dispersed in the polymer.

The admixing of the bioactive agent and the polymer can be carried out with or without an additional solvent (other than the polymer). In one aspect, the admixing can be accomplished without the use of an additional solvent (other than the polymer). Thus, in this aspect, a solvent removal step is not required after the admixing step.

The amount of bioactive agent incorporated into the composition varies depending upon a particular drug, the desired therapeutic effect and the desired time span. Because a variety of compositions are intended to provide dosage regimens for therapy for a variety of purposes, there is no critical lower or upper limit in the amount of drug incorporated into the composition. The lower limit will generally depend upon the activity of the drug and the time span of its release from the device. Those skilled in the pharmaceutical arts can determine toxic levels of a given drug as well as the minimum effective dose.

Various forms of the bioactive agent can be used, which are capable of being released from polymer into a subject. A liquid or solid bioactive agent can be incorporated into the compositions described herein. The bioactive agents can be water soluble or water-insoluble. In some aspects the bioactive agent may be moderately water soluble, and is preferably only slightly or very slightly water soluble. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, prodrug, or other form to provide the effective biological or physiological activity.

Examples of bioactive agents that can be incorporated into the compositions herein include, but are not limited to, small molecules, peptides, proteins such as hormones, enzymes, antibodies, antibody fragments, antibody conjugates, nucleic acids such as aptamers, iRNA, siRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents. Bioactive agents contemplated for use in the disclosed compositions include anabolic agents, antacids, anti-asthmatic agents, anti-cholesterolemic and anti-lipid agents, anticoagulants, anti-convulsants, anti-diarrheals, anti-emetics, anti-infective agents including antibacterial, anitviralantiviral and antimicrobial agents, anti-inflammatory agents, anti-manic agents, anti-metabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate, morphine, mineral supplements, cholestryramine, N-acetylprocainamide, acetaminophen, acetylsalicylic acid, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents in the compositions include, but are not limited to, peptide drugs, protein drugs, therapeutic antibodies, desensitizing materials, antigens, anti-infective agents such as antibiotics, antimicrobial agents, antiviral, antibacterial, antiparasitic, antifungal substances and combinations thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampicin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, loratadine and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; anti-psychotics such as haloperidol, risperidone, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth hormone releasing factor, angiotensin, FSH, EGF, bone morphogenic protein (BMP), erythropoietin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as ranitidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens, Neisseria meningitides, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgdorferi, Campylobacter jejuni*, and the like; antigens of such viruses as smallpox, influenza A and B, respiratory syncytial, parainfluenza, measles, HIV, SARS, varicella-zoster, herpes simplex 1 and 2, cytomegalovirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcus neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed, or attenuated, organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Timidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The compositions, as discussed above, can be used in a variety of applications, such as cosmetics, agriculture, pharmaceuticals, among others. In one specific aspect, the compositions can be used as pharmaceutical compositions. For pharmaceutical compositions, the releasable agent will generally be a bioactive agent, but does not have to be. For example, the releasable agent can be a non-bioactive substance and still be used in a pharmaceutical composition. A variety of pharmaceutical compositions comprising the polymer and agent can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the agent into association with a carrier or a finely divided solid carrier, or both. In some aspects, the polymer itself can be the carrier and/or can be combined with other carriers or additives. Other pharmaceutical carriers can also be used. Examples of solid carriers, other than the polymer (if solid), include lactose, terra alba, sucrose, talc, gelatin, agar, pectin, acacia, magnesium stearate, and stearic acid. Examples of liquid carriers, other than the polymer (if liquid), are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, or a salt.

Certain polymers of the present invention (e.g., polymers with higher molecular weights) may be waxy and thus not injectable. However, these alkyl substituted polylactides can still retain the desirable property of being very hydrophobic and lipophilic in comparison to normal polylactide and polylactide-co-glycolide polymers, thus having an advantage for many applications, including pharmaceutical applications. In some aspects, certain polymers can exhibit better control of drug release, but are not necessarily injectable. Thus, in certain embodiments, a non-injectable alkyl substituted polylactide can be made injectable by admixing a plasticizer or other substance with the alkyl substituted polylactide. In a further aspect, a non-injectable alkyl-substituted polylactide can be made injectable by reducing the viscosity of the polymer, for example, with an additive as discussed above, or by heating just prior to administering the injection.

In one aspect, the composition can be present in a kit. The kit can comprise a suitable package or container for the compositions. Examples include without limitation sterile packaging. Because the disclosed compositions are suitable for use as injectable compositions, a kit can include a prepackaged injection device, comprising an injection device that is loaded with the composition. Suitable injection devices include without limitation syringes, trochars, and others.

As discussed above, the compositions can be used to administer a bioactive agent to a subject in need thereof, for example to treat a disorder for which the bioactive agent is effective. The compositions can be administered to any tissue or fluid of a subject. Likewise, the mode of administration can be any suitable mode, for example parental administration, oral administration, enteral administration, topical administration and the like. In some aspects, the liquid compositions comprising one or more low viscosity polymers can be injected into a subject. The nature of the composition administered will generally be selected based on the desired dosage of the bioactive agent, which will vary greatly depending on the disorder but can be readily determined by one experienced in the pharmaceutical arts.

An "effective amount" of a composition refers to an amount of the composition that will achieve a desired therapeutic result. Thus, the effective amount will vary greatly depending on the composition, bioactive agent, and disorder or condition that is being treated. The actual effective amount of dosage amount of the composition administered to a subject can be determined by physical and physiological factors such as body weight, severity of condition, the type of disease being treated, previous or concurrent therapeutic interventions, idiopathy of the patient and can depend on the route of administration. Depending upon the dosage and the route of administration, the number of administrations of a preferred dosage and/or an effective amount may vary according to the response of the subject. One of skill in the art can determine an effective amount of a disclosed pharmaceutical composition.

In some non-limiting examples, a dose can comprise from about 0.01 microgram/kg/body weight, about 0.1 microgram/kg/body weight, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 100 mg/kg/body weight, about 5 microgram/kg/body weight to about 500 milligram/kg/body weight, etc., can be administered, based on the numbers described above.

In one aspect, the polymers can be used to alter the pharmacokinetics of a bioactive agent. For example, the polymers can be used to reduce the degradation of a bioactive agent. The polymers can also be used to provide more complete, or better controlled, (e.g., as compared to polylactide) release of the bioactive into a subject.

The compositions can be administered to any desired subject. The subject can be a vertebrate, such as a mammal, a fish, a bird, a reptile, or an amphibian. The subject of the herein disclosed methods can be a mammal, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In some aspects the subject is a mammal. In some aspects the subject is a human. The compositions can also be administered by any suitable route, including parenterally, topically, orally, enterally, bucally, rectally, sublingually, mucosally, or by inhalation among others. In one aspect the composition is administered orally. In a further aspect the composition is administered enterally. In a further aspect the composition is applied topically. In a further aspect the composition is administered parenterally. Parenteral administration includes, but is not limited to, intraveneous, intradermal, intramuscular, intraarterial, intrathecal, subcutaneous, intraperitonial, intravitreal administration. In one aspect, the composition can be injected into a subject. The invention is further illustrated by the following non-limiting examples.

EXAMPLES

Example 1

Synthesis of 2-Hydroxyoctanoic Acid

To 78 g NaHSO$_3$ (0.75 mol) in 1 L water, 57 g heptaldehyde (0.5 mol) were added and vigorously stirred for 30 min, then a solution of 32 g NaCN (0.65 mol) in 250 mL water was added, and the mixture was stirred for another 15 min. The upper layer upon separation of phases was poured directly into 165 mL of 40 v % sulfuric acid and heated at 125° C. for 3 h, then poured into 500 mL 6N NaOH (for safety: the cooled solution was slowly poured into the sulfuric acid in an ice bath controlling the temperature), and stirred for 12 h at room temperature. The alkaline solution was washed twice with Et$_2$O (150 mL), then acidified with 2M HCl, and extracted thrice with Et$_2$O (150 mL). The combined latter Et$_2$O phases were washed with 100 mL brine, dried, and afterwards the solvent distilled off. Recrystallization from toluene gave 47 g of pure product: 59% yield. $^1$H NMR (500 MHz, CDCl$_3$): d 4.28 (dd, 1H), 1.65-1.9 (br m, 2H), 1.4-1.5 (br m, 2H), 1.25-1.35 (br m, 6H), 0.89 (t, 3H). 13C NMR (500 MHz, CDCl$_3$): d 180.00, 70.3, 34.11, 31.59, 28.89, 24.67, 22.53, 14.00.

Example 2

Polymerization of 2-Hydroxyoctanoic Acid Using Tin(II) 2-Ethylhexanoate

Tin(II) 2-ethylhexanoate (Sn(Oct)$_2$) was used to polymerize 2-hydroxyoctanoic acid. For the polymerization reaction of 12.0 g (75 mmol) of 2-hydroxyoctanoic acid, 0.153 g (3.8 mmol; 0.5 mol % cat.), tin(II) 2-ethylhexanoate were filled into a round-bottom flask followed by addition of the monomer. The flask was connected to a micro-distillation bridge and a vacuum pump. The polymerization was started by heating in a preheated oil-bath to 180° C. under permanent stirring and by increasing the vacuum over 30 minutes to a typical oil-pump vacuum of around 0.001 bar. These conditions were maintained throughout the entire polycondensation reaction. At the desired reaction end, the flask was cooled down to 20° C. and the crude compound was dissolved in 20 mL acetone. The solution was added dropwise into 0.5 L of a cold (4° C.) mixture of 10% (v/v) water in ethanol under stirring and was further precipitated at 4° C. for 24 hours.

The solution was decanted off and the precipitated polymer was dissolved in acetone and centrifuged for 10 minutes. The supernatant containing the polymer was collected and the solvent was evaporated. Residual solvents were removed at 150° C. under vacuum for 3 hours.

During the first 16 hours of a 12 g scale polycondensation using tin(II) 2-ethylhexanoate (0.5 mot-%) as catalyst at 180° C., the molecular weight of the product hexyl-substituted poly(lactic acid) polymer ("HEX-PLA") increases linearly (FIG. 1). The weight-average molecular weight (M$_w$) was 1120 g/mol after one hour, 5070 g/mol after four hours and 20,220 g/mol after 16 hours. The M$_w$ for a smaller 2.5 g scale reaction under the same reaction conditions lead to 53,190 g/mol after 24 hours (Table 1).

TABLE 1

HEX-PLA melt polycondensation with tin(II) 2-ethylhexanoate (Sn(Oct)$_2$) as polycondensation catalyst.

| Time (h) | Temperature (° C.) | Monomer mass (g) | Catalyst (mol-%) | M$_w$ (g/mol) | PDI |
|---|---|---|---|---|---|
| 24 | 180 | 2.5 | 0.5 | 53,190 | 1.52 |
| 24 | 180 | 2.5 | 0.75 | 47,510 | 1.52 |
| 24 | 180 | 2.5 | 1.0 | 42,410 | 1.45 |
| 24 | 180 | 2.5 | 2.0 | 38,260 | 1.52 |

The polydispersities (PD) were around 1.5 for all reactions. A time dependent molecular weight control for hex-PLAs up to 20,000 g/mol was observed. All melt polycondensations yielded viscous and clear, but yellowish-colored polymers, appearing more pronounced with harsher reaction conditions.

Example 3

Polymerization of 2-Hydroxyoctanoic Acid Using Sulfuric Acid

Sulfuric acid was used to polymerize 2-hydroxyoctanoic acid. For the polymerization reaction of 7.0 g (44 mmol) of 2-hydroxy octanoic acid, 0.022 g (2.2 mmol; 0.5 mol % cat.) sulfuric acid (96%) were filled into a round-bottom flask followed by addition of the monomer. The flask was connected to a micro-distillation bridge and a vacuum pump. The polymerization was started by heating in a preheated oil-bath to 150° C. under permanent stirring and by increasing the vacuum over 30 minutes to a typical oil-pump vacuum of around 0.001 bar. These conditions were maintained throughout the entire polycondensation reaction. At the desired reaction end, the flask was cooled down to 20° C., and the crude compound was dissolved in 20 mL acetone. The solution was added drop-wise into 0.5 L of a cold (4° C.) 0.1 M NaHCO$_3$-solution under stirring and was further precipitated at 4° C. for 24 h.

The solution was decanted off and the precipitated polymer was dissolved in acetone and transferred into a round bottom flask for removal of acetone and residual water under vacuum. The polymer was again dissolved in acetone and filtered through Celite® 545 coarse. Residual solvents were removed from the purified product at 150° C. under vacuum for 3 hours.

Sulfuric acid has good water solubility which can facilitate polymer purification by precipitation into water. Under slightly basic conditions (e.g., addition of 0.1 M NaHCO$_3$) non-reacted monomers become water soluble and can be fully removed. Melt polycondensations catalysed with sulfuric acid and purified with water can lead to pure, clear and colorless, viscous polymers.

Figure 2:
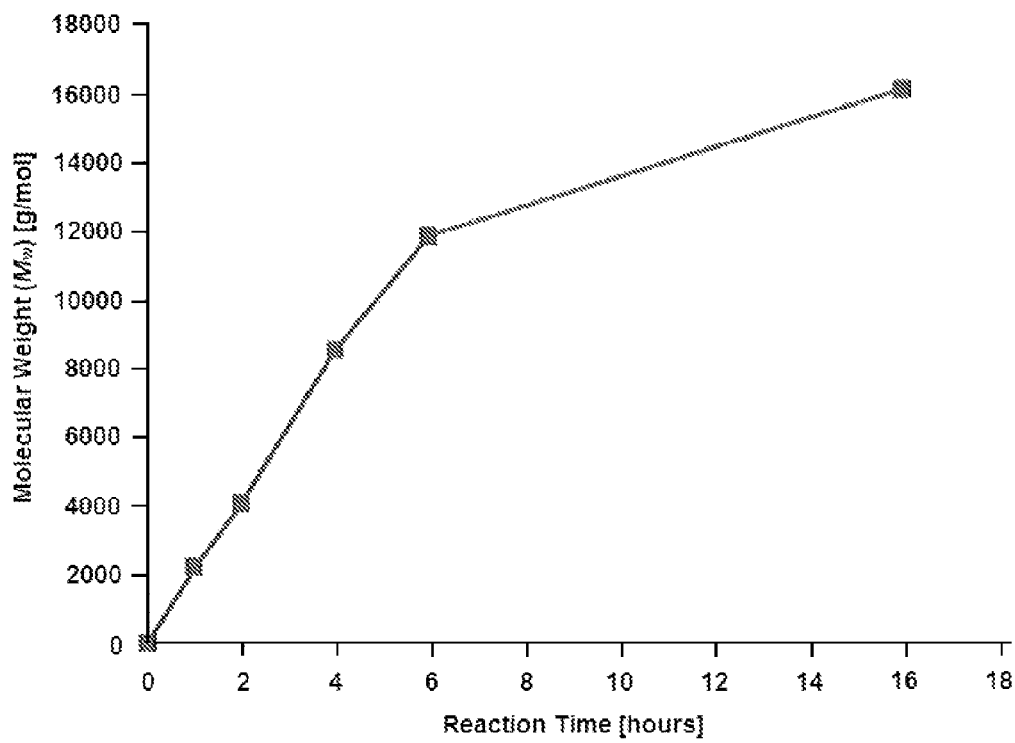
FIG. 2 is a plot of molecular weight versus reaction time for the polymerization of 2-hydroxyoctanoic acid using sulfuric acid as a catalyst.

With a mean batch size of 7.0 g and a reaction temperature of 150° C., polymers with molecular weights up to 11,820 g/mol (Table 2) could be obtained. Higher reaction temperatures of 180° C. led to a similar M$_w$, but led to higher impurities. A lower reaction temperature of 120° C. led to a decrease in M$_w$ (7000 g/mol). As observed for Sn(Oct)$_2$, the catalyst concentration of sulfuric acid influences the M$_w$. Concentrations lower than 0.5 mol-% sulfuric acid lead to a decrease in M$_w$. Larger batches (21.0 g in comparison to 7.0 g) gave lower M$_w$. Sulfuric acid catalysed melt polycondensations facilitate the synthesis of defined molecular weights by controlling the reaction time (FIG. 2). A linear increase in M$_w$ was observed during the first 6 hours, followed by a reduced $M_w$ increase and leading to a $M_w$ of up to 20,000 g/mol for longer reaction times. For all sulfuric acid catalysed melt polycondensations, high yields of 90% of pure colorless hexPLAs were obtained after the aqueous precipitation procedure.

TABLE 2

HEX-PLA melt polycondensation with sulfuric acid as polycondensation catalyst (7.0 g scale)

| Time (h) | Temp. (° C.) | Catalyst (mol %) | $M_n$ (g/mol) | $M_w$ (g/mol) | PDI | Viscosity (Pa's) at 25° C. | at 37° C. |
|---|---|---|---|---|---|---|---|
| 6 | 120 | 0.50 | 4,430 | 7,000 | 1.58 | 20.0 | 8.0 |
| 6 | 150 | 0.50 | 8,140 | 11,820 | 1.45 | 41.7 | 16.0 |
| 6 | 180 | 0.50 | 7,480 | 10,670 | 1.43 | 26.3 | 10.6 |
| 6 | 150 | 0.16 | 2,240 | 3,600 | 1.61 | 21.7 | 8.4 |
| 6 | 150 | 0.80 | 3,620 | 7,100 | 1.96 | 27.9 | 10.9 |
| 1 | 150 | 0.50 | 1,640 | 2,180 | 1.33 | 31.3 | 11.2 |
| 2 | 150 | 0.50 | 2,830 | 4,050 | 1.43 | 24.6 | 9.4 |
| 4 | 150 | 0.50 | 6,170 | 8,530 | 1.38 | 35.0 | 13.4 |
| 6 | 150 | 0.50 | 8,140 | 11,820 | 1.45 | 37.2 | 14.6 |
| 8 | 150 | 0.50 | 8,050 | 12,030 | 1.49 | nd | nd |
| 16 | 150 | 0.50 | 7,590 | 16,030 | 2.11 | nd | nd | nd: not determined

Example 4

Polymerization of 2-Hydroxyoctanoic Acid in Large Scale Using Sulfuric Acid

Sulfuric acid was used to polymerize 2-hydroxyoctanoic acid. For the polymerization reaction of 21.0 g (132 mmol) of 2-hydroxy octanoic acid, 0.066 g (6.6 mmol; 0.5 mol % cat.) sulfuric acid (96%) were filled into a round-bottom flask followed by addition of the monomer. The flask was connected to a micro-distillation bridge and a vacuum pump. The polymerization was started by heating in a preheated oil-bath to 120° C. under permanent stirring and by increasing the vacuum over 30 minutes to a typical oil-pump vacuum of around 0.001 bar. These conditions were maintained throughout the entire polycondensation reaction. At the desired reaction end, which was either after 2 hours, 6 hours, or 16 hours, the flask was cooled down to 20° C., and the crude compound was dissolved in 20 mL acetone. The solution was added drop-wise into 2 L of a cold (4° C.) 0.1 M NaHCO$_3$-solution under stirring and was further precipitated at 4° C. for 24 h.

The solution was decanted off and the precipitated polymer was dissolved in acetone and transferred into a round bottom flask for removal of acetone and residual water under vacuum. The polymer was again dissolved in acetone and filtered through Celite® 545 coarse. Residual solvents were removed from the purified product at 120° C. under vacuum for 1 hour.

With this method a molecular weight of 2,000 g/mol was obtained for a polymerization time of 2 h, 4,000 g/mol for 6 h and 10,000 g/mol for a 16 h reaction time.

Figure 3:
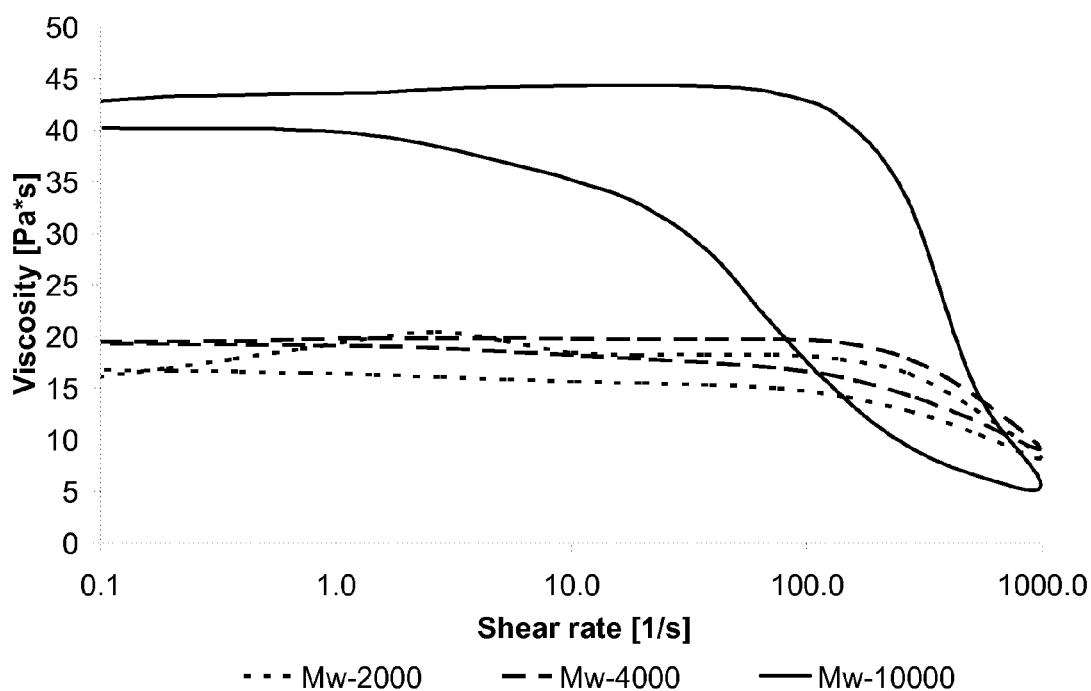
FIG. 3 is a plot of viscosity versus shear rate for polymers prepared by melt polycondensation of 2-hydroxyoctanoic acid of different molecular weight

The rheological behavior of the three polymers was assessed using a rheometer (Bohlin Instruments CVO 120 high res, Bohlin Instruments, USA) in a 20 mm parallel plate set-up with a gap size of 1 mm. The temperature was maintained at 25° C. and the shear rate was varied in the range between 0.1 l/s and 1000 l/s. FIG. 3 shows the viscosity over shear rate for all three polymers. The polymers show shear-thinning behavior at shear rates higher than 100 l/s and also thixotropy.

Example 5

Catalyst-Free Polymerization of 2-Hydroxyoctanoic 15.0 g (94 mmol) of 2-hydroxy octanoic acid were filled into a round-bottom flask and the flask was connected to a micro-distillation bridge and a vacuum pump. The polymerization was started by heating in a preheated oil-bath to 120° C., or 150° C. under permanent stirring and by increasing the vacuum over 30 minutes to a typical oil-pump vacuum of around 0.001 bar. These conditions were maintained throughout the entire polycondensation reaction. At the desired reaction end, which was either after 6 hours, or 8 hours, the reaction was stopped by cooling the flask down to 20° C. The obtained polymer was not further purified since no additional catalyst had been used. The polymer was sterilized with a dry heat method by warming it to a temperature of 180° C. for 30 min. The weight average molecular weight and the PDI were determined by gel permeation chromatography.

With a mean batch size of 15.0 g and a reaction temperature of 150° C., polymers with molecular weights up to 1720 g/mol (Table 3) were obtained. Increase in reaction time from 6 hours to 8 hours lead to an increase in $M_w$. Lower reaction temperatures of 120° C., with a reaction time of 8 hours led to slightly higher $M_w$ (1890 g/mol).

TABLE 3

HEX-PLA catalyst-free melt polycondensation (15.0 g scale)

| Time [h] | Temp. [° C.] | Mw [g/mol] | PDI |
|---|---|---|---|
| 6 | 150 | 1510 | 1.35 |
| 8 | 150 | 1720 | 1.71 |
| 8 | 120 | 1890 | 1.47 |
| 8 | 120 | 1850 | 1.35 |

Example 6

Modification of the Viscosity by Addition of Plasticizers

Figure 4:
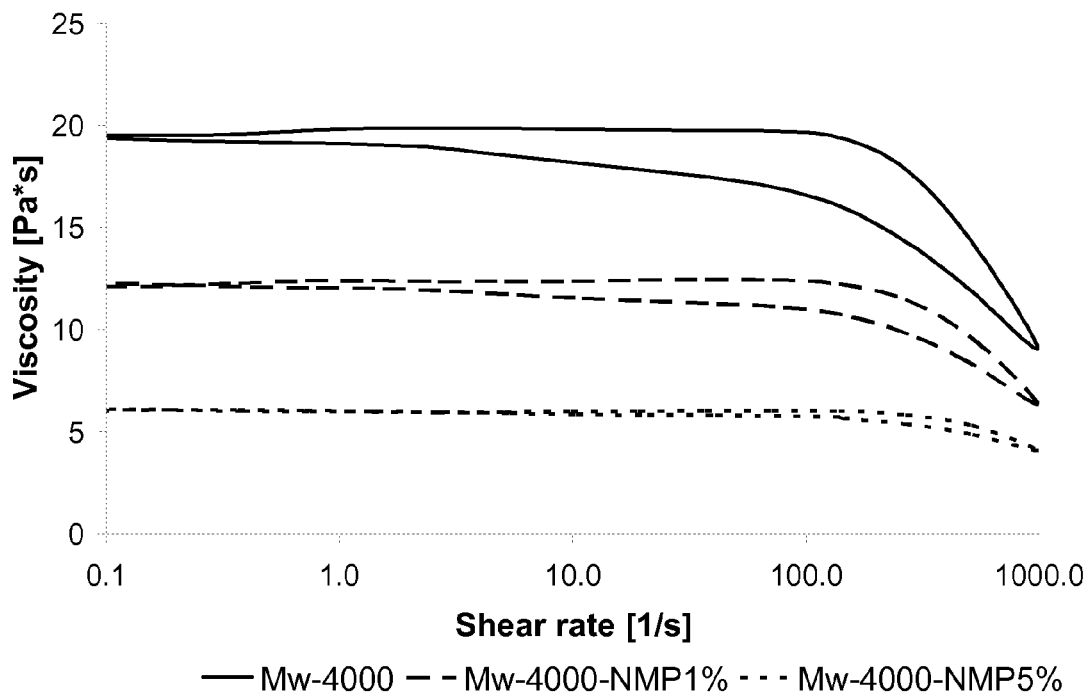
FIG. 4 is a plot of viscosity versus shear rate for a neat polymer prepared by melt polycondensation of 2-hydroxyoctanoic acid, and the polymer blended with 1% and 5% NMP

To the polymer of example 4 having a molecular weight of 4,000 g/mol the plasticizer N-methylpyrrolidone (NMP) was added in quantities of 1% and 5% (m/m), respectively, by mixing polymer and plasticizer at room-temperature in a small sealed plastic bag. The rheological behavior was measured using a rheometer (Bohlin Instruments CVO 120 high res, Bohlin Instruments, USA) in a 20 mm parallel plate set-up with a gap size of 1 mm. FIG. 4 illustrates that the viscosity can efficiently be reduced by the addition of small amounts of plasticizer, while the overall rheological behavior with shear-thinning and thixotropy remains unaffected.

Example 7

Injectability of hexPLA and Formulations with NMP

Figure 5:
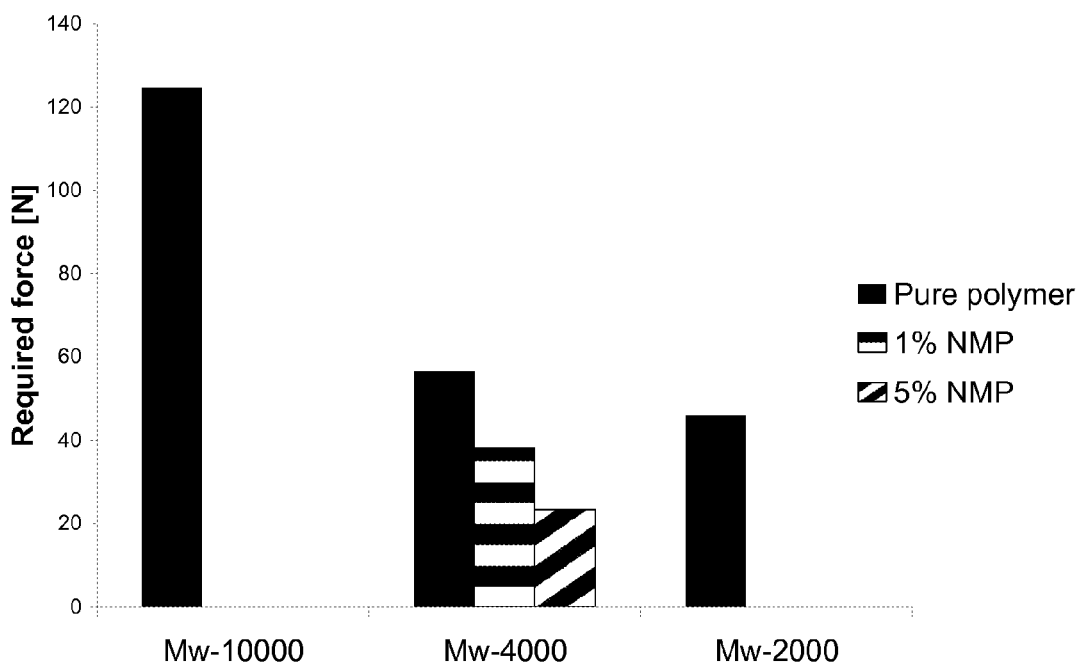
FIG. 5 is a graph of the required injection force for native polymer, and for polymers blended with 1% and 5% NMP

The pure polymers from example 4 with a molecular weight of 2,000 g/mol, 4,000 g/mol, and 10,000 g/mol as well as the mixtures with 1% and 5% NMP from example 6 were filled into 2 mL Omnifix luer-lock syringes (B. Braun Melsungen, Germany). Each syringe was connected to an ENOSA hollow-needle (1.2×50 mm, ROSE, Germany). The maximal force needed to eject the viscous material from the syringes was measured at a plunger speed of 0.5 cm/min. The values are summarized in FIG. 5 showing that the injectability of hexPLA is better with lower molecular weights. It is seen from FIG. 5 that to further improve the ease of injection small amounts of NMP are sufficient.

Example 8

Incorporation and Release of Haloperidol

Figure 6:
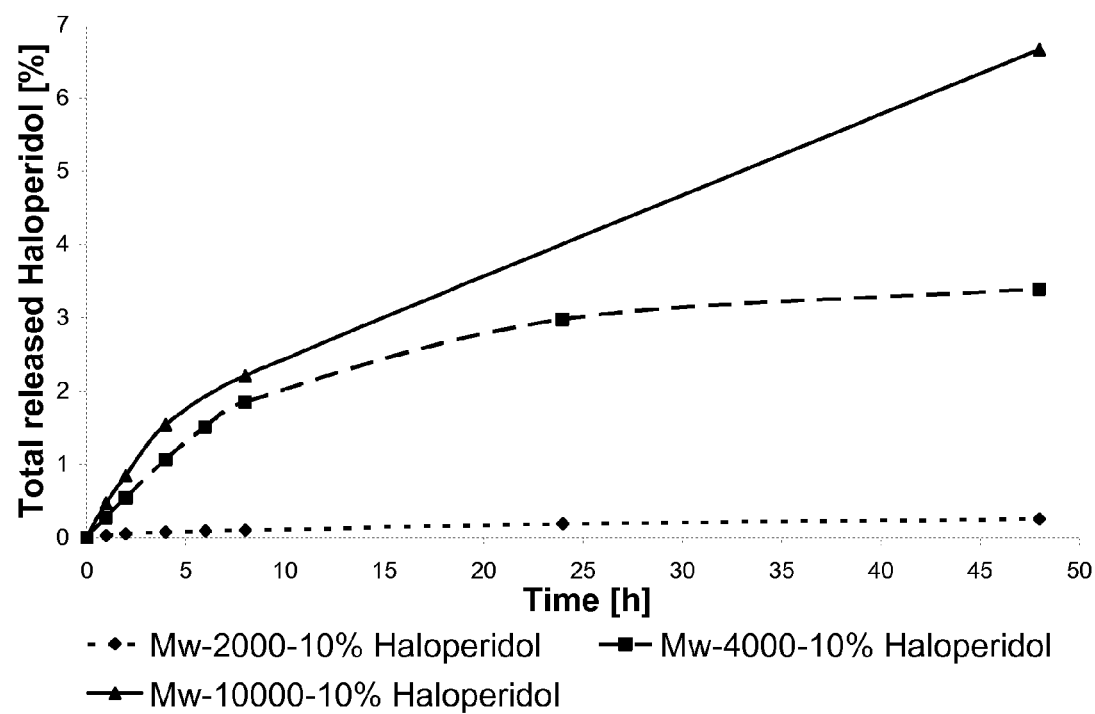
FIG. 6 is a plot of in vitro haloperidol release from polymers prepared by melt polycondensation of 2-hydroxyoctanoic acid of different molecular weight

10% (m/m) Haloperidol (Sigma-Aldrich Chemie GmbH, Germany), as an exemplary small molecule releasable agent, were incorporated into the three polymers of example 4 by kneading the Haloperidol and hexPLA in a sealed plastic bag at room-temperature until a homogenous suspension was obtained as confirmed by optical microscopy. From each of the three formulations 0.1 g were placed into 40 mL of Citrate-Phosphate-Buffer pH 5.0. The samples were incubated at 120 rpm and 37° C. and samples of the release medium were taken at certain timepoints over 48 hours. The Haloperidol in the release samples was quantified by UV-spectroscopy at 249 nm. FIG. 6 displays the release of Haloperidol from formulations with hexPLA. A steady release of Haloperidol from the formulations over 48 hours is observed with the amount of released drug depending on the molecular weight of the polymer. The formulation having a molecular weight of 2,000 g/mol showed the slowest release in comparison to the formulations with higher molecular weight because Haloperidol is dissolvable in the hexPLA matrix and the solubility also is depending on the molecular weight.

The invention claimed is:

1. A pharmaceutical formulation obtained by a process comprising combining a poly(hydroxyalkyl acid) polymer prepared by melt polycondensation of one or more substituted or unsubstituted $C_4$-$C_{32}$ 2-hydroxyalkyl acid(s) with a bioactive molecule, or excipients, or pharmaceutically acceptable carriers or adjuvants, or particles, or a combination thereof, wherein the said poly(hydroxyalkyl acid) polymer is a homopolymer of 2-hydroxyalkyl acid, or a block copolymer comprising a 2-hydroxyalkyl acid homopolymer polymerized with a poly(ethylene glycol) (PEG) block.

2. A pharmaceutical composition comprising a poly(hydroxyalkyl acid) polymer having a polydispersity index of at least 1.35 prepared by melt polycondensation of one or more substituted or unsubstituted $C_4$-$C_{32}$ 2-hydroxyalkyl acid and excipients, and at least one bioactive molecule or pharmaceutically acceptable carrier or adjuvant, or particle, wherein the poly(hydroxyalkyl acid) polymer is entirely free from cyclic monomers, wherein the average molecular weight of the poly(hydroxyalkyl acid) polymer is less than about 5,000 Daltons and wherein the poly(hydroxyalkyl acid) polymer is a homopolymer of $C_4$-$C_{32}$ 2-hydroxyalkyl acid or a block copolymer comprising $C_4$-$C_{32}$ 2-hydroxyalkyl acid copolymerized with a poly(ethylene glycol) (PEG) block.

3. The pharmaceutical composition according to claim 2, wherein the PEG is a methoxypoly(ethylene glycol).

4. The pharmaceutical composition according to claim 2, wherein the pharmaceutical composition is injectable.

5. The pharmaceutical composition according to claim 2, wherein the pharmaceutical composition is a topical or oral formulation.

6. The pharmaceutical composition according to claim 2, wherein the bioactive molecule is a releasable bioactive molecule.

7. The pharmaceutical composition according to claim 2, wherein the poly(hydroxyalkyl acid) polymer is a D-2-hydroxyoctanoic acid, a L-2-hydroxyoctanoic acid, or a D,L-2-hydroxyoctanoic acid polymer.

8. A method for delivering a bioactive agent to a subject comprising administering to the subject an effective amount of the composition of claim 2.

9. The pharmaceutical composition according to claim 2, wherein the poly(hydroxyalkyl acid) polymer is entirely free from substituted or unsubstituted lactides, glycolides or caprolactones.

10. The pharmaceutical composition according to claim 2, wherein the poly(hydroxyalkyl acid) polymer has a polydispersity index of at least 1.48.

11. The pharmaceutical composition according to claim 2, wherein said poly(hydroxyalkyl acid) polymer is liquid.

12. The pharmaceutical composition according to claim 7, wherein said poly(hydroxyalkyl acid) polymer is liquid.

13. The pharmaceutical composition according to claim 2, wherein said bioactive molecule is selected from androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate, morphine, mineral supplements, cholestryramine, N-acetylprocainamide, acetaminophen, acetylsalicylic acid, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

* * * * *